United States Patent [19]

Thompson

[11] 4,402,943

[45] Sep. 6, 1983

[54] ANTIHYPERTENSION TREATMENT

[75] Inventor: Ralph B. Thompson, Oak Brook, Ill.

[73] Assignee: T & R Chemicals, Inc., Clint, Tex.

[21] Appl. No.: 337,114

[22] Filed: Jan. 5, 1982

[51] Int. Cl.$^3$ .................. A61K 31/70; A61K 31/095; A61K 31/115

[52] U.S. Cl. .................................. 424/180; 424/333; 424/334; 424/335

[58] Field of Search ............... 424/180, 162, 333, 334, 424/335; 536/122

[56] References Cited

U.S. PATENT DOCUMENTS

| | | |
|---|---|---|
| 2,367,302 | 1/1945 | Moore . |
| 3,836,639 | 9/1974 | Teler .................................... 424/101 |
| 3,906,109 | 9/1975 | Roehm ................................ 424/325 |
| 4,327,083 | 4/1982 | Alvarez ............................... 424/162 |

OTHER PUBLICATIONS

Merck Index, 9th Ed., 1976, No. 4094.
Chao, Thrombos, Haemostas (Stuttg), vol. 35, 1976, pp. 717–736.
Shulman, Chem. Abs., vol. 47, 1953, p. 9386.
Gunnison, Fd. Cosmet. Toxicol., vol. 19, 1981, pp. 667–682.
Elias, Abstract of Thromb. Diath Haemorrh, vol. 18(3–4), 1967, pp. 499–509.
Torda, Abs. of Anaesth. Intens. Care, 1, 293, (1973).
Bourbon, Abs. of J. Eur. Toxicol., vol. 4, No. 3, pp. 205–207, (1971).
Chem. Abs., 9th Coll. Index, p. 37336CS & vol. 82, Ab. No. 107247f, (1975).
Kikugawa, J. Pharm. Sci., vol. 61, 1972, pp. 1904–1907.
Rost, "Comparative Invst. of the Pharmacol. Effects of Organically Bonded Sulfurous Acids and of Neutral Sodium Sulfite", in Arb. A. D. Kaiserlichen Gesundheitsamte, vol. 21, 1904, p. 312.

Primary Examiner—Anna P. Fagelson
Attorney, Agent, or Firm—Cushman, Darby & Cushman

[57] ABSTRACT

The treatment of mammals with addition products of a carbonyl group containing compound with bisulfites to improve a mammal (including man) suffering from hypertension is described.

6 Claims, No Drawings

ANTIHYPERTENSION TREATMENT

BACKGROUND OF THE INVENTION

Jose Antonio Arias Alvarez has previously discovered that inorganic salts of sulfurous acid (especially sodium bisulfite) are antihypertensive agents. See U.S. application, Ser. No. 75,423, filed Sept. 14, 1979, now U.S. Pat. No. 4,327,083 issued Apr. 27, 1982.

Sodium bisulfite (usually shown by formula to be NaHSO$_3$) has heretofore been used for many commercial purposes, such as a preservative for prevention of the deterioration of liquid systems, such as food stuffs and of pharmaceutical solids, and has also been used medically both externally, such as for treatment of parasitic skin diseases, and internally such as for a gastrointestinal antiseptic. So far as now known, sodium bisulfite has never previously been used by man for the treatment of hypertension.

The solid sodium bisulfite of commerce reportedly consists chiefly of sodium metabisulfite, Na$_2$S$_2$O$_5$, and sodium bisulfite, and, for purposes of this invention, such is believed to possess the same properties as (and to be equivalent to) sodium bisulfite when dissolved in aqueous solution.

BRIEF SUMMARY OF THE INVENTION

There has now been discovered a class of active organic agents, the members of which when introduced by ingestion, injection, absorption, or otherwise into a mammal (including man), produce avoidance, amelioration and/or improvement of a hypertensive condition in mammals and man when used in an antihypertensively effective amount as taught herein.

The active antihypertensive agents of the present invention are salts of carbonyl sulfur dioxide adducts which display anticoagulant and antithrombotic activity. Presently preferred agents are representable by the formula:

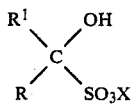

(1)

where:
R is a radical selected from the group consisting of hydrogen and hydroxymethyl,
R$^1$ is a radical selected from the group consisting of hydrogen, straight chain alkyl radicals each containing a total of 2, 3, 4, or 5 hydroxylated carbon atoms, and a residue from a polysaccharide capable of reducing Fehling's solution,
X is selected from the group consisting of alkali metals and ammonium.

One presently preferred compound of formula (1) is sodium formaldehyde bisulfite. Sodium is presently preferred as X.

The term "monosaccharide" as used herein has reference to an organic compound which is an hydroxyaldehyde or an hydroxyketone which contains an hydroxyl group on a carbon adjacent to a carbonyl group. The term "polysaccharide" as used herein has reference to a saccharide which contains more than one monosaccharide in its structure. Polysaccharides and monsaccharides useful in this invention are each capable of reducing Fehling's solution. For present purposes, a one gram quantity of a saccharide is dissolved or dispersed in 25 grams of distilled water, and 5 milliliters of Fehling's solution is added thereto. If there is a precipitate of cuprous oxide formed upon standing or upon warming to 50° C. then the saccharide is usable in the practice of this invention as a starting material.

A presently preferred class of starting materials comprises monosaccharides, each having a carbonyl group, which are selected from the group consisting of aldoses and ketoses wherein each ketose has its carbonyl group in the 2-position. More preferred such monsaccharides each contain five or six carbon atoms per molecule. Presently preferred aldoses are selected from the group consisting of glucose, mannose, ribose, xylose, arabinose, galactose, and the like.

Another preferred class of starting materials comprises polysaccharides, such as a dextrin prepared by acid treatment of starch, maltose, cellobiose, lactose, melibiose, manninotriose, and the like.

In one aspect, the present invention is directed to the use of certain organic carbonyl-type bisulfite compounds as antihypertensive agents in human medicine.

In another aspect, the present invention is directed to a method for control of, and/or prevention of, hypertension in man by oral ingestion and/or injection of a pharmacologically effective amount of saccharide bisulfites and/or compound(s) within the scope of the active agents of this invention.

In another aspect, the present invention leads to symptomatic and objective improvement in a cardiovascular disease condition, such as hypertension in man. By the term "symptomatic improvement", as used herein, reference is had to an improvement in a patient's subjective symptoms as reported by that patient. By the term "objective improvement", as used herein, reference is had to a measurable and objective change in the patient's condition (e.g. blood pressure), from an initial (at the start of treatment) to a subsequent (during or after treatment) condition.

Naturally, an active antihypertensive agent of this invention is used, if at all in a mammal, at a pharmaceutically effective dose rate, that is, at a dose rate which is below the level of toxicity or of production of undesired side effects. Because of biological complexities, the complete biological effects of the active agents of this invention are not now known.

Other and further aspects, objects, purposes, advantages, aims, utilities, features, and the like will be apparent to those skilled in the art from a reading of the present specification.

DETAILED DESCRIPTION

More particularly, this invention concerns a process for treating a human to control, ameliorate, or prevent a cardiovascular disease such as hypertension wherein there is introduced, preferably orally, into such a human a pharmaceutically effective amount of an active agent of this invention as defined above (preferably a bisulfite).

In one preferred mode of using this invention, an aqueous solution of from about 1 to 15% by weight active agent is prepared. Then such solution is orally consumed by a human, for example, in the form of drops, at a total (or accumulated) dose rate ranging from 0.2 to 20 mg per each kilogram of body weight per day, more preferably in the form of from two to four spaced doses per day, each such dose being preferably taken around meal time.

Symptomatic and/or objective improvement in a patient's hypertensive condition even at relatively low dosage rates may occur within two weeks to four months of such a continuous oral usage of active agent in accord with these teachings of this invention.

Such dilute active agent solutions can be used before, during, or after the onset of a cardiovascular disease with beneficial results. Even when used on patients who might be considered terminally affected by such condition, beneficial results are observable.

It is believed that larger and/or smaller such doses can be used without departing from the spirit and scope of the present discovery. One dose rate, for example, which has usually been found to be effective for man varies from about 0.2 to 75 mgm per day per average human adult patient (e.g. about 70 kg) of active agent taken orally as dilute aqueous solution of from about 1 to 5 percent by weight in distilled water and ingested before, during or after each of the daily meals, such as breakfast, lunch, and dinner. Presently, a preferred dose rate for a patient using a self-administered dilute aqueous system comprises one in the range from about 1.0 to 20 mgm per kg of body weight per day taken in the form of at least two spaced oral doses (using such an aqueous solution as described herein). The water used in such a solution is preferably purified (e.g. filtered, deionized, distilled or the like). After preparation, such a solution is preferably stored in a closed container.

Such an aqueous solution can be directly consumed by a patient as drops (e.g. from about 5 to 20 drops per meal, depending upon dose rate for an individual patient), or as a capsule, or the like, as desired.

A subjective improvement in atherosclerosis may be observable by some patients who have been dosed as described above. It may be that use of this invention exerts a favorable influence on blood lipids, such as a fall in total cholesterol.

One important advantage of the present invention is the circumstance that the indicated desirable results may be achieved with little or no apparent side effects surprisingly. For example, no change in a normal excretion rate of such metallic ions as sodium, potassium, magnesium, or calcium through urine appears to be associated with the use of active agents of this invention, contrary to normal experience with conventional diuretic agents which are used to lower blood pressure.

The active agents of this invention can be administered by any convenient or appropriate procedure. For example, injection by intravenous, intraperitoneal, intramuscular or subcutaneous administration of such a dilute aqueous solution as described above may afford a more rapid reduction in blood pressure than is observable from oral administration for reasons which are not presently known. Suppositories containing active agents can be used for absorption.

The active agents of the present invention can be formulated in any desired manner for administration. For example, conventional excipients, extenders, compounding agents and the like can be blended with powdered active agents and the resulting blends can be tableted, pelletized, or the like and then used as solid oral dosage forms. Conveniently, individual dosage units, in whatever form prepared or compounded, can range from about 50 to 500 milligrams (mg) each.

Per diem (24 hour day) dose rates for active agents of this invention for mammals (including man) are believed to range from about 0.2 to 50 mg per kg of body weight, with doses ranging from about 1 to 20 mg per kg being more general, convenient and typical for practical, safe administration. Larger and smaller dose rates can be employed without departing from the spirit and scope of this invention.

One convenient preparation technique for preparing a saccharide/bisulfite compound of formula (1) above is to agitate a saturated aqueous solution of the desired bisulfite salt with at least a stoichiometric amount of a carbonyl compound which corresponds to the desired carbonyl sulfur dioxide adduct desired. In the case of monsaccharide adducts, one or more equivalents of the sugar is (are) mixed with an equivalent of the bisulfite compound in aqueous medium to provide a solution of the bisulfite adduct of the sugar. Solutions containing more than about 60 weight percent water are preferred. Other known synthetic methods may be used if desired in order to obtain the saccharide-bisulfite compounds as solids as for oral ingestion.

Aqueous solutions represent a practical way of practicing this invention. The agents of this invention do not oxidize readily in air-exposed aqueous solutions.

In one preferred mode of using this invention, an aqueous solution containing from about 1 to 10 percent by weight of an active agent of this invention, preferably sodium glucose bisulfite or sodium formaldehyde bisulfite, is used. Then, such solution is injected into, or orally consumed by, a patient at total (or accumulated) dose rate preferably ranging from about 1.0 to 50 mg per each kg of body weight per day, more preferably in the form of at least two spaced doses per day, and still more preferably in the form of at least three spaced dose per day, such a dose being preferably taken around meal time. Solid or encapsulated active agents may be orally consumed alternatively.

One presently preferred composition for use in the practice of this invention is prepared by dissolving a desired quantity of an alkali metal bisulfite in an aqueous glucose solution, such as a standardized medical solution of about 5 weight percent glucose in distilled water (of the type used for intravenous administration to a patient).

The active agents used in any aqueous solution can be directly used in accordance with the teachings of this invention, in which such a solution can be dispensed dropwise, or such a solution can be encapsulated, or the like, and used as measured dosage units, as desired. For example, an aqueous solution containing 5 weight percent of sodium glucose bisulfite or sodium formaldehyde bisulfite can be injected into a patient or it can be directly consumed by a patient as drops (e.g., from about 5 to 30 drops per meal for each of the two or three meals eaten by such patient per day, depending upon an individual patient's body weight, or the like).

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF ACTIVE AGENTS

Example A

A solution of sodium formaldehyde bisulfite is prepared by dissolving commercially available solid sodium formaldehyde bisulfite in distilled water at room temperature to form a 3 percent by weight aqueous solution.

Example B

Another solution of sodium formaldehyde bisulfite is prepared by dissolving commercially available solid sodium formaldehyde bisulfite in distilled water at room temperature to form a 10 percent by weight aqueous solution.

Example C

A capsule of sodium formaldehyde bisulfite is prepared by charging to each of standard gelatin capsules sufficient sodium formaldehyde bisulfite to make 25 mg of active agent.

Example D

The procedure of Example C is repeated except that 50 mg capsule of active agent are prepared.

Example E

A solution to contain 2% by weight of sodium bisulfite is prepared by dissolving the desired amount of bisulfite with one equivalent of glucose.

Example F

The procedure of Example E is repeated except that four equivalents of glucose are used.

Example G

The procedure of Example F is repeated except that the product is heated on a steam bath (about 90° C.) for one hour.

Example H

The procedure of Example E is repeated except that in place of glucose, fructose is used.

Example I

The procedure of Example E is repeated except that in place of glucose arabinose is used.

Examples 1

To demonstrate effectiveness of an agent of the present invention, experiments were carried out with hypertensive rats.

Rats of the SHR (spontaneous hypertensive rat) strain, weighing about 250 g, were anesthetized with urethane (ethyl carbamate) using 1500 milligrams per kilogram IP. The trachea was cannulated to avoid respiratory distress and the body temperature maintained constant with a heated pad controlled from a rectal sensor. The carotid artery was cannulated with a fine nylon catheter connected to a Honeywell blood pressure transducer filled with heparinized saline. The mean and phasic blood pressures were recorded on a Devices F19 multi-channel recorder. Test substances were administered by the intraperitoneal route, unless otherwise stated. Soluble materials were given as aqueous solutions and insoluble materials as emulsions or suspensions in aqueous vehicles. The test substances were given at a series of increasing dose levels each subsequent dose being twice the previous dose. The results quoted in the Table give the lowest dose level firstly to cause a clear lowering of blood pressure and secondly the dose found to cause the death by the preparation.

TABLE I

| | Hypertensive and Toxic Dose Levels of Sulfite Derivatives | | |
|---|---|---|---|
| Substance | Route of Administration | Hypertensive Dose Level mg/kg | Toxic Dose Level mg/kg |
| Sodium Glucose Sodium Bisulfite | IP | 20 | Not Obtained |

Clearly the sodium glucose bisulfite lowers blood pressure.

I claim:

1. A method of treating hypertension in a human suffering from said condition comprising introducing into said human an antihypertensively effective amount of at least one compound of the formula:

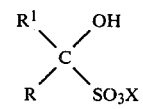

where:
R is a radical selected from the group consisting of hydrogen and hydroxymethyl,
$R^1$ is a radical selected from the group consisting of hydrogen and straight chain alkyl radicals each containing a total of 2, 3, 4, or 5 hydroxylated carbon atoms, and a residue from a polysaccharide capable of reducing Fehling's solution, and
X is selected from the group consisting of alkali metals and ammonium.

2. The method of claim 1 wherein said compound is sodium glucose bisulfite.

3. The method of claim 1 wherein said compound is sodium formaldehyde bisulfite.

4. The method of claim 1 in which the amount of said compound is from about 0.2 to about 50 mg per kg of body weight per day.

5. The method of claim 4 wherein the amount of said agent is about 1 to about 20 mg per kg of body weight per day.

6. The method of claim 1 in which said agent is administered in divided doses of at least two doses per day.

* * * * *